US012668564B2

(12) United States Patent
Yoo et al.

(10) Patent No.: US 12,668,564 B2
(45) **Date of Patent: *Jun. 30, 2026**

(54) METHOD FOR PREPARING BIS(GLYCOL)TEREPHTHALATE AND POLYESTER RESIN USING SAME

(71) Applicant: SK CHEMICALS CO., LTD., Gyeonggi-do (KR)

(72) Inventors: Young-Man Yoo, Gyeonggi-do (KR); Eun-Yeong Hwang, Gyeonggi-do (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/724,617

(22) PCT Filed: Mar. 23, 2023

(86) PCT No.: PCT/KR2023/003857

§ 371 (c)(1),
(2) Date: Jun. 27, 2024

(87) PCT Pub. No.: WO2023/195668

PCT Pub. Date: Oct. 12, 2023

(65) Prior Publication Data

US 2025/0066283 A1 Feb. 27, 2025

(30) Foreign Application Priority Data

Apr. 5, 2022 (KR) ........................ 10-2022-0042550

(51) Int. Cl.

*C07C 67/03* (2006.01)
*C08G 63/06* (2006.01)
*C08J 11/24* (2006.01)

(52) U.S. Cl.

CPC .............. *C07C 67/03* (2013.01); *C08G 63/06* (2013.01); *C08J 11/24* (2013.01); *C08J 2367/06* (2013.01)

(58) Field of Classification Search

CPC ......... C07C 67/03; C07C 69/82; C08G 63/06; C08G 63/183; C08G 63/199; C08G 63/672; C08G 63/78; C08J 11/24; C08J 2367/06

See application file for complete search history.

(56) References Cited

FOREIGN PATENT DOCUMENTS

| | | | |
|---|---|---|---|
| CN | 112625221 | * | 4/2021 |
| JP | 2000-169623 | A | 6/2000 |
| JP | 2005089572 | * | 4/2005 |
| KR | 2001-0095884 | A | 11/2001 |
| KR | 100336534 | * | 5/2002 |
| KR | 10-2004-0101800 | A | 12/2004 |
| KR | 10-2013-0120906 | A | 11/2013 |
| KR | 10-2018-0024320 | A | 3/2018 |
| KR | 10-2020-0061948 | A | 6/2020 |
| KR | 20200061948 | * | 6/2020 |
| KR | 10-2021-0037267 | A | 4/2021 |

OTHER PUBLICATIONS

Ganesan et al. (An overview on the recent advances in the transesterification of vegetable oils for the biodiesel production using chemical and biocatalysts, Rev. Environ. Sci. Biotechnol., 8, pp. 367-394, Published 2009) (Year: 2009).*
Mahata et al. (Poly(butylene adipate-co-terephthalate) Polyester Synthesis Process and Product Development, Polymer Sciences, Series C, 63, 1, pp. 102-111. Published 2021) (Year: 2021).*
KR100336534 translation (Year: 2002).*
KR20200061948 translation (Year: 2020).*
JP2005089572 translation (Year: 2005).*
Sang Ho Park et al., Poly (ethylene terephthalate) recycling for high value added textiles, Fashion and Textiles, 2014, pp. 1-17, 1:1, Springer.
International Search Report for the International Application No. PCT/KR2023/003857 issued by the International Searching Authority (Korean Intellectual Property Office) on Jun. 26, 2023.
Office Action for Korean Patent Application No. 10-2022-0042550 issued by the Korean Patent Office on Apr. 21, 2026.

* cited by examiner

*Primary Examiner* — Andrew D Kosar
*Assistant Examiner* — Blaine G Doletski
(74) *Attorney, Agent, or Firm* — IP & T GROUP LLP

(57) ABSTRACT

Through a transesterification reaction in which a predetermined amount of bis(2-hydroxyethyl)terephthalate relative to glycol is fed in a divided or continuous manner, bis (glycol)terephthalate with a low residual amount of an ethylene glycol derivative is prepared, and polyester engineering products or biodegradable polyester products with high crystallinity can be produced therefrom.

10 Claims, 1 Drawing Sheet

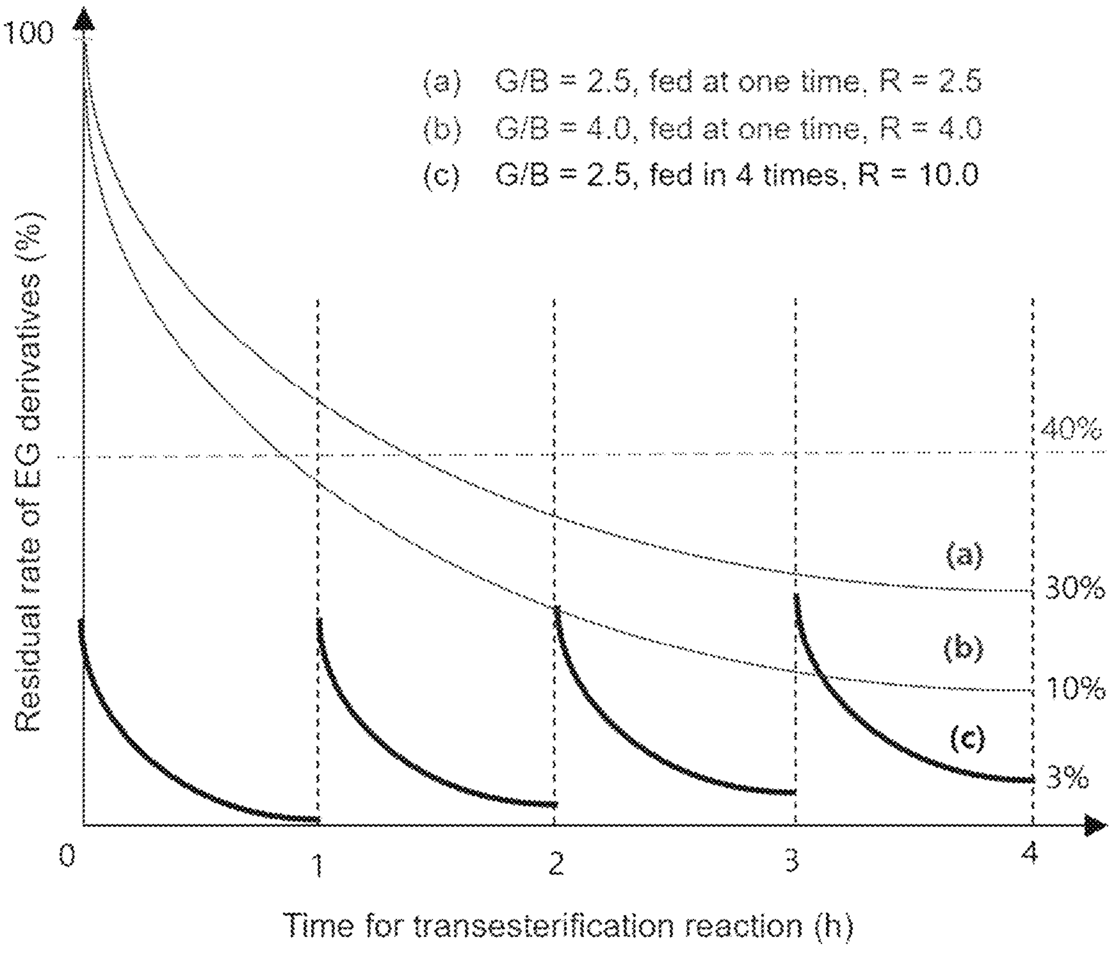
100
(a) G/B = 2.5, fed at one time, R = 2.5
(b) G/B = 4.0, fed at one time, R = 4.0
(c) G/B = 2.5, fed in 4 times, R = 10.0
Residual rate of EG derivatives (%)
40%
(a)
30%
(b)
10%
(c)
3%
0
1
2
3
4
Time for transesterification reaction (h)

METHOD FOR PREPARING BIS(GLYCOL)TEREPHTHALATE AND POLYESTER RESIN USING SAME

This application is a national stage application of PCT/KR2023/003857 filed on Mar. 23, 2023, which claims priority of Korean patent application number 10-2022-0042550 filed on Apr. 5, 2022. The disclosure of each of the foregoing applications is incorporated herein by reference in its entirety.

TECHNICAL FIELD

The present invention relates to the preparation of a bis(glycol)terephthalate using regenerated monomers and to polyester resins and articles obtained therefrom.

BACKGROUND ART

Polyester is widely used as a material for beverage-filling containers, packaging films, audio and video films, and the like by virtue of its excellent mechanical strength, thermal resistance, transparency, and gas barrier properties. In addition, polyester is widely produced worldwide as an industrial material such as medical fibers and tire cords. In particular, polyester sheets or plates have good transparency and excellent mechanical strength, so that they are widely used as raw materials for cases, boxes, partitions, shelves, panels, packaging materials, building materials, interior and exterior materials, and the like.

As a result, waste of plastics such as polyester is generated globally at an unmanageable level every year. Recently, countries around the world are preparing regulations and plans for recycling waste plastic resources, including waste polyester. Although physical or chemical methods are used as methods of recycling waste polyester, physical recycling methods cannot guarantee purity and are not widely used.

In chemical recycling methods, the ester bond of waste polyester is broken to depolymerize it. Reactions such as glycolysis, hydrolysis, methanolysis, and aminolysis are used. Glycolysis among them is to decompose waste polyester by adding a glycol such as ethylene glycol or diethylene glycol at high temperatures. For example, bis(2-hydroxyethyl) terephthalate (BHET) can be obtained through the glycolysis of waste polyethylene terephthalate (PET), and a technique of using it as a raw material for preparing a polyester resin is known.

However, from the viewpoint of environmental friendliness, it is more meaningful to convert waste PET products, which generally have a short lifespan, into engineering polyester products or environmentally friendly biodegradable polyester products that have a long lifespan. In this regard, recently, attempts have been made to regenerate polyester resins other than PET through the transesterification of waste PET and glycol. Since an excessive amount of a glycol is used in this reaction and the reaction time is long, there is a problem in that a large amount of by-products such as cyclic ester compounds are formed as a side reaction of the glycol.

Prior Art Document (Non-patent Document 1) Park, S. H., Kim, S. H., Poly (ethylene terephthalate) recycling for high value added textiles, Fashion and Textiles 1, 1 (2014)

DISCLOSURE OF INVENTION

Technical Problem

The present inventors have attempted to develop a method capable of minimizing the formation of by-products without using an excessive amount of a glycol through a technology to recycle BHET obtained by the depolymerization of waste PET-based products into various engineering polyester products or environmentally friendly biodegradable polyester products.

Meanwhile, recycled BHET has generally low purity due to impurities formed from the reagents used in the depolymerization process and side reactions, so that high-cost processes such as ion exchange or recrystallization are required to purify it, making it difficult to be commercially utilized.

As a result of research to solve this problem, it has been possible to obtain a bis(glycol) terephthalate with high purity, while using BHET with low purity or reducing the amount of a glycol used, by feeding BHET in a divided or continuous manner to a transesterification reaction with various glycols. As a result, it has been possible to manufacture a variety of engineering polyester products with high quality or environmentally friendly biodegradable polyester products.

Accordingly, an object of the present invention is to prepare a bis(glycol) terephthalate with high purity by using recycled BHET without using an excessive amount of a glycol and to provide various polyester resins and articles with high quality therefrom.

Solution to Problem

According to an aspect of the present invention, there is provided a process for preparing a bis(glycol) terephthalate, which comprises (1) feeding at least one glycol component having 3 or more carbon atoms to a reactor; and (2) feeding bis(2-hydroxyethyl) terephthalate to the reactor in a divided or continuous manner and carrying out a transesterification reaction, wherein the following Relationship (1) is satisfied:

$$1.0 \leq G/B \leq 3.5 \quad (1)$$

In Relationship (1), G is the total number of moles of the at least one glycol component, and B is the total number of moles of the bis(2-hydroxyethyl) terephthalate.

According to another aspect of the present invention, there is provided a process for preparing a polyester resin, which comprises (1) feeding at least one glycol component having 3 or more carbon atoms to a reactor; (2) feeding bis(2-hydroxyethyl) terephthalate to the reactor in a divided or continuous manner and carrying out a transesterification reaction; and (3) subjecting the product of the transesterification reaction to a polycondensation reaction, wherein the above Relationship (1) is satisfied:

According to another aspect of the present invention, there is provided a polyester resin prepared by the above process.

According to another aspect of the present invention, there is provided an article, which comprises the polyester resin.

Advantageous Effects of Invention

According to the present invention, a bis(glycol) terephthalate, which is a platform for various polymers, can be prepared through the transesterification of BHET and a glycol. In particular, it is advantageous in terms of cost since the purity can be enhanced, while using BHET with low purity or reducing the amount of a glycol used, as a certain amount of BHET, relative to the glycol, is introduced into the reaction in a divided or continuous manner.

In particular, since the residual amount of ethylene glycol derivatives in the bis(glycol) terephthalate recycled according to the present invention is low, a polyester resin having high crystallinity can be produced. Thus, it is possible to produce high value-added engineering polyester products or biodegradable polyester products with low ethylene glycol components that affect ecotoxicity from waste PET products.

BRIEF DESCRIPTION OF DRAWINGS

FIG. 1 shows the change in the residual rate of ethylene glycol derivatives over time with respect to the feeding method during a transesterification reaction.

BEST MODE FOR CARRYING OUT THE INVENTION

Hereinafter, the present invention will be described in more detail.

In this specification, terms referring to the respective components are used to distinguish them from each other and are not intended to limit the scope of the embodiment. In addition, in the present specification, a singular expression is interpreted to cover a plural number as well unless otherwise specified in the context.

In the present specification, the terms first, second, and the like are used to describe various components. But the components should not be limited by the terms. The terms are used for the purpose of distinguishing one element from another.

In the present specification, the term "comprising" is intended to specify a particular characteristic, region, step, process, element, and/or component. It does not exclude the presence or addition of any other characteristic, region, step, process, element and/or component, unless specifically stated to the contrary.

The molecular weight of a compound or polymer described in the present specification, for example, a number average molecular weight or a weight average molecular weight, is a relative mass based on carbon-12 as is well known. Although its unit is not described, it may be understood as a molar mass (g/mole) of the same numerical value, if necessary.

In the present specification, a "derivative" of a specific compound refers to a compound obtained by partially transforming the compound through a chemical reaction or combining it with other components, thereby containing the main part of the compound.

In the present specification, a unit or group "derived" from a specific component refers to a part of the component contained in a final product through a chemical reaction such as a polymerization reaction. It may be present in a form in which a part thereof is modified during the reaction or it is combined with other components. For example, a unit or group derived from at least one monomer is contained in the chain constituting a polymer.

According to an aspect of the present invention, there is provided a process for preparing a bis(glycol) terephthalate, which is a platform for various polymers, through the transesterification of bis(2-hydroxyethyl) terephthalate and a glycol.

The process for preparing a bis(glycol) terephthalate comprises (1) feeding at least one glycol component having 3 or more carbon atoms to a reactor; and (2) feeding bis(2-hydroxyethyl) terephthalate to the reactor in a divided or continuous manner and carrying out a transesterification reaction.

Glycol Component

The glycol component used in the present invention is employed in a transesterification reaction with bis(2-hydroxyethyl) terephthalate to form a residue in a bis(glycol) terephthalate as a product. It constitutes the polymer chain of a final polyester resin polymerized from the bis(glycol) terephthalate.

The glycol component used in the present invention may be a glycol having 3 or more carbon atoms for substituting an ethylene glycol residue in a transesterification reaction.

In particular, the glycol component has a boiling point higher than that of ethylene glycol by 10° C. or more, which is advantageous for purification through fractional distillation during the transesterification reaction.

Specifically, the glycol component used in the transesterification reaction of the present invention may be a glycol monomer other than ethylene glycol (e.g., alkylene glycol having 3 or more carbon atoms) or a polymer glycol (e.g., polyether).

As a more specific example, the glycol component may be at least one selected from glycol monomers having 3 to 10 carbon atoms and having a molecular weight of less than 250 and polymeric glycols having a number average molecular weight of 400 to 5,000.

The number of carbon atoms of the glycol monomer may be, for example, 3 or more or 4 or more, and may be 15 or less, 12 or less, 10 or less, or 8 or less.

As a specific example, the glycol monomer may be an alkylenediol having 3 to 10 carbon atoms. In addition, the glycol monomer may be an aliphatic alkylenediol.

As a specific example, the glycol monomer may be selected from the group consisting of 1,3-propanediol, 1,4-butanediol, 1,4-cyclohexanedimethanol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 2,3-butanediol, 3-methyl-1,5-pentanediol, 3-methyl-2,4-pentanediol, 1,6-hexanediol, 1,2-cyclohexanediol, 1,4-cyclohexanediol, and diethylene glycol.

As a more specific example, the glycol monomer comprises at least one selected from 1,3-propanediol, 1,4-butanediol, and 1,4-cyclohexanedimethanol and may optionally further comprise other glycol monomers.

The glycol monomer may have a molecular weight of, for example, less than 400, less than 350, less than 300, or less than 250.

The polymer glycol may be, for example, selected from the group consisting of polyethylene glycol, polypropylene glycol, polytetramethylene glycol, polyhexamethylene glycol, copolymers of ethylene oxide and tetrahydrofuran, ethylene oxide-adducted polypropylene glycol, polycarbonatediol, polyneopentyl glycol, poly-3-methylpentanediol, and poly-1,5-pentanediol. More specifically, the polymer glycol may be at least one selected from the group consisting of polytetramethylene glycol, polycarbonatediol, polypropylene glycol, and ethylene oxide-adducted polypropylene glycol.

The polymer glycol may have a number average molecular weight of, for example, 400 or more, 500 or more, 600 or more, 700 or more, or 800 or more, and may be 6,000 or less, 5,000 or less, 4,000 or less, or 3,000 or less. As a specific example, the number average molecular weight of the polymer glycol may be 400 to 5,000. More specifically, it may preferably be 1,000 to 3,000 from the viewpoint of the reduction in phase separation.

The polymer glycol is used in an amount of 5% by weight to 75% by weight, specifically, 10% by weight to 60% by weight, more specifically, 15% by weight to 50% by weight, based on the weight of a final polyester resin, which is advantageous for achieving a high molecular weight while improving the elasticity of the polyester resin.

Bis(2-Hydroxyethyl) Terephthalate

In bis(2-hydroxyethyl)terephthalate used in the present invention, an ethylene glycol residue is substituted with a glycol residue having 3 or more carbon atoms through a transesterification reaction. Bis(2-hydroxyethyl) terephthalate is an ester of two ethylene glycols and one terephthalic acid. For example, it is a compound formed as an intermediate in the process of preparing a polyester such as polyethylene terephthalate (PET) through the polymerization of ethylene glycol and terephthalic acid or its ester.

The bis(2-hydroxyethyl) terephthalate used in the present invention may be obtained by the depolymerization of waste polyester. For example, the bis(2-hydroxyethyl) terephthalate may be obtained from waste polyester having a repeat unit of ethylene glycol and terephthalic acid like polyethylene terephthalate (PET) or glycol-modified polyethylene terephthalate (PETG). Specifically, it may be obtained by well-known depolymerization methods such as glycolysis, hydrolysis, and methanolysis. In particular, the bis(2-hydroxyethyl) terephthalate may be obtained by depolymerizing waste polyethylene terephthalate with ethylene glycol and then purifying it.

Recycled bis(2-hydroxyethyl) terephthalate obtained by the depolymerization of waste polyester as described above (referred to as recycled BHET or abbreviated as r-BHET or rBHET) may contain reagents or solvents used in various chemical steps during the depolymerization of waste polyester, or by-products formed by side reactions with them. Thus, BHET recycled by a common depolymerization process contains organic and inorganic impurities in addition to BHET as the main component; thus, its purity is not high. Since recycled BHET generally contains trace amounts of organic and inorganic impurities in addition to BHET as the main component, recycled BHET can also be viewed as a kind of composition comprising two or more components, i.e., a BHET composition.

Impurities contained in the recycled BHET may comprise, for example, diethylene glycol derivatives and unreacted monomers. The total content of impurities contained in the recycled BHET may be 10% by weight or more, 15% by weight or more, or 20% by weight or more, and may be 40% by weight or less, 35% by weight or less, 30% by weight or less, or 25% by weight or less.

The purity of the recycled BHET may be measured using liquid chromatography or the like. Specifically, the purity of the recycled BHET may be calculated by measuring the fraction (%) of the peak area of BHET out of the total peak area in a spectrum obtained using high-performance liquid chromatography (HPLC).

For example, the purity of the recycled BHET may be 90% or less, 85% or less, or 80% or less, and may be 60% or more, 65% or more, or 70% or more. Specifically, the purity of the BHET introduced into the transesterification reaction of the present invention may be 60% to 90%, more specifically, 65% to 85% or 70% to 80%.

Acid Component

According to the present invention, an acid component may be further introduced during the transesterification reaction. Specifically, in step (1), at least one acid component selected from dicarboxylic acids and esters and anhydrides thereof may be additionally fed to the reactor.

Specifically, the dicarboxylic acid may be at least one selected from aliphatic dicarboxylic acids and aromatic dicarboxylic acids.

As an example, the dicarboxylic acid may comprise an aliphatic dicarboxylic acid. Specifically, the aliphatic dicarboxylic acid may be a linear, branched, or cyclic aliphatic dicarboxylic acid. The number of carbon atoms of the aliphatic dicarboxylic acid may be 4 or more, 5 or more, 6 or more, or 7 or more, and may be 20 or less, 15 or less, 13 or less, 12 or less, or 10 or less. As a specific example, the number of carbon atoms of the aliphatic dicarboxylic acid may be 4 to 20 or 4 to 12.

The aliphatic dicarboxylic acid may be, for example, selected from the group consisting of adipic acid, sebacic acid, succinic acid, isodecylsuccinic acid, maleic acid, fumaric acid, glutaric acid, azelaic acid, 1,4-cyclohexanedicarboxylic acid, and 1,3-cyclohexanedicarboxylic acid, but it is not limited thereto.

As another example, the dicarboxylic acid may comprise an aromatic dicarboxylic acid. The number of carbon atoms of the aromatic dicarboxylic acid may be 6 or more, 7 or more, 8 or more, or 10 or more, and may be 25 or less, 20 or less, or 15 or less. As a specific example, the number of carbon atoms of the aromatic dicarboxylic acid may be 8 to 20 or 8 to 14.

The aromatic dicarboxylic acid may be, for example, selected from the group consisting of terephthalic acid, isophthalic acid, naphthalenedicarboxylic acids such as 2,6-naphthalenedicarboxylic acid, diphenyl dicarboxylic acid, 4,4'-stilbendicarboxylic acid, 2,5-furandicarboxylic acid, 2,5-thiophenedicarboxylic acid, but it is not limited thereto.

Meanwhile, the additional acid component may be a dicarboxylic acid or an ester thereof other than terephthalic acid, and it may constitute a copolymerization unit together with a unit derived from bis(2-hydroxyethyl) terephthalate during polycondensation after the transesterification reaction.

As a specific example, the dicarboxylic acid may comprise adipic acid to enhance the biodegradability of a final polyester resin. To this end, adipic acid or an alkyl ester thereof, specifically dimethyl adipate, may be used as an acid component in the present invention. For example, the total amount of adipic acid and an alkyl ester thereof may be 70% by weight to 99% by weight based on the weight of the entire acid components.

In addition, the dicarboxylic acid may further comprise an aliphatic dicarboxylic acid component, an aromatic dicarboxylic acid component, or a mixture thereof, other than adipic acid. In such an event, the total amount of the dicarboxylic acid other than adipic acid may be 1% by weight to 30% by weight based on the weight of the entire acid components.

Transesterification Reaction

The glycol and bis(2-hydroxyethyl) terephthalate are subjected to a transesterification reaction.

[Reaction Scheme 1]

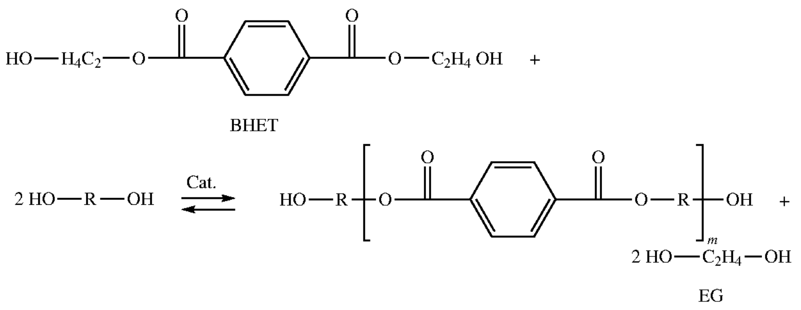

In Reaction Scheme 1, m is an integer of 1 to 4.

The transesterification reaction may be carried out in the presence of a catalyst. Thus, when the glycol component and the acid component or bis(2-hydroxyethyl) terephthalate are fed to the reactor, a catalyst may be fed together.

As the catalyst for the transesterification reaction, for example, at least one selected from the group consisting of a titanium-based catalyst, a germanium-based catalyst, an antimony-based catalyst, an aluminum-based catalyst, and a tin-based catalyst may be used.

Examples of the titanium-based catalyst include tetraethyl titanate, acetyltripropyl titanate, tetrapropyl titanate, tetrabutyl titanate, 2-ethylhexyl titanate, octylene glycol titanate, triethanolamine titanate, acetylacetonate titanate, ethylacetoacetic ester titanate, isostearyl titanate, titanium dioxide, and the like. Examples of the germanium-based catalyst include germanium dioxide, germanium tetrachloride, germanium ethylene glycol oxide, germanium acetate, or combinations thereof. Specifically, germanium dioxide can be used as the germanium-based catalyst. Both crystalline and amorphous germanium dioxide may be used as the germanium dioxide, and glycol-soluble ones may also be used.

The amount of the transesterification catalyst employed may vary depending on the reaction conditions and the catalyst used. As an example, a metal-based catalyst (e.g., titanium-based catalyst, tin-based catalyst) may be employed such that the metal weight of the metal-based catalyst is 0.0001% by weight to 0.005% by weight based on the total weight of the glycol and bis(2-hydroxyethyl) terephthalate fed to the reactor.

The transesterification reaction may be carried out in a batch or continuous type.

As an example, when a glycol component, or a glycol component with an acid component, is collectively fed to a reactor, and the temperature reaches a certain level while the temperature is raised, bis(2-hydroxyethyl) terephthalate may be fed. The feeding of bis(2-hydroxyethyl) terephthalate may be carried out, for example, while ethylene glycol as a by-product is removed in a nitrogen atmosphere at a temperature of 180° C. to 280° C.

According to the present invention, bis(2-hydroxyethyl) terephthalate is introduced into the transesterification reaction with a glycol component in a divided or continuous manner.

According to an embodiment, bis(2-hydroxyethyl) terephthalate is introduced into the transesterification reaction with a glycol component in a divided manner of two or more times.

The number of divided introductions may be 2 times or more, 3 times or more, 4 times or more, or 5 times or more, and may be 100 times or fewer, 50 times or fewer, 30 times or fewer, 20 times or fewer, 15 times or fewer, or 10 times or fewer. As a specific example, the number of divided introductions may be 2 to 30 times or 3 to 15 times.

The time interval between the divided introductions may be determined by dividing the total introduction time by the number of divided introductions. The total introduction time may be, for example, 1 hour or longer or 2 hours or longer, and may be 5 hours or shorter or 4 hours or shorter.

In addition, the amount of introduction at one time during the divided introductions may be determined by dividing the total amount of bis(2-hydroxyethyl) terephthalate to be introduced into the reaction by the number of divided introductions.

According to the present invention, the components introduced into the transesterification reaction satisfy the following Relationship (1).

$$1.0 \leq G/B \leq 3.5 \qquad (1)$$

In Relationship (1), G is the total number of moles of the at least one glycol component, and B is the total number of moles of the bis(2-hydroxyethyl) terephthalate.

If G/B is less than 1.0, there are many ethylene glycol residues derived from BHET, which may deteriorate the physical properties of a final polyester resin. If G/B exceeds 3.5, an excessive amount of a glycol component is fed, which is not preferable. For example, G/B may be 1.0 or more, 1.5 or more, or 2.0 or more, and may be 3.5 or less, 3.0 or less, or 2.5 or less. As a specific example, G/B may be 1.0 to 3.0, 1.0 to 2.5, or 1.5 to 2.5.

The number of divided introductions and the total introduction amount may be more effectively controlled by the following Relationship (2). As an example, the introduction ratio (R) of bis(2-hydroxyethyl) terephthalate according to Relationship (2) may be 5 or more.

$$R = G \times \frac{N}{B} \qquad (2)$$

In Relationship (2), G is the total number of moles of the at least one glycol component, B is the total number of moles of the bis(2-hydroxyethyl) terephthalate, and N is the number of divided introductions of the bis(2-hydroxyethyl) terephthalate.

For example, the R value may be 5 or more, 6 or more, 8 or more, or 10 or more, and may be 100 or less, 50 or less, 30 or less, or 20 or less. As a specific example, it may be 4 to 50 or 6 to 30.

FIG. 1 shows the change in the residual rate of ethylene glycol derivatives over time with respect to the feeding method during a transesterification reaction.

Referring to FIG. 1, (a) if it is introduced at one time with a G/B set to 2.5 (i.e., R=2.5), the amount of ethylene glycol derivatives (mainly BHET) decreases as the reaction progresses from the maximum (100%) at the beginning of the introduction; however, even at the time of completion of the reaction, the residual rate of ethylene glycol derivatives remains at a high level (30%); (b) if it is introduced at one time with a G/B set to 4.0 (i.e., R=4.0), the amount of ethylene glycol derivative decreases more steeply and reaches a low level (10%) at the time of completion of the reaction; and (c) if it is introduced as divided in 4 times with a G/B set to 2.5 (i.e., R=10.0), the amount of ethylene glycol derivative is maintained at a certain level (40%) or less throughout the entire reaction process, and, especially, it reaches a very low level (3%) at the time of completion of the reaction.

In (a) and (b) of FIG. 1, as conventional methods, an excessive amount of a glycol component is required to lower the residual rate of the final ethylene glycol derivatives, which increases the cost. In contrast, in (c), as a method of the present invention, the residual amount of ethylene glycol derivatives in the final product may be at a very low level even without increasing the amount of a glycol component.

According to another embodiment, bis(2-hydroxyethyl) terephthalate is introduced into the transesterification reaction with a glycol component in a continuous manner.

The total time of continuous introduction may be, for example, 1 hour or longer or 2 hours or longer, and may be 5 hours or shorter or 4 hours or shorter.

For example, the continuous introduction may be to introduce a constant amount of bis(2-hydroxyethyl) terephthalate per hour. The amount of introduction per hour may be determined by dividing the total amount of bis(2-hydroxyethyl) terephthalate to be introduced into the reaction by the total introduction time.

As a specific example, bis(2-hydroxyethyl) terephthalate may be dissolved in water at about 80 to 100° C. to prepare an aqueous BHET solution having a concentration of about 10 to 20% by weight, which may be continuously introduced. The continuous introduction may be carried out from the beginning of the transesterification reaction until one hour before the completion of the reaction. A dropping funnel may be used at the laboratory level, or a metered feeder may be used at the commercial level, for the continuous introduction of a constant amount per hour.

When the introduction of bis(2-hydroxyethyl) terephthalate in a divided or continuous manner is completed, the reaction conditions may be maintained until the transesterification reaction is completed. In addition, a process of removing ethylene glycol as a by-product may be continued during the transesterification reaction. The removal of ethylene glycol may be carried out by a distillation process using a difference in boiling point from other components. Ethylene glycol thus distilled off may be recovered by cooling and reused in other processes.

The termination point of the transesterification reaction may be determined by considering the theoretical amount of ethylene glycol formed from bis(2-hydroxyethyl) terephthalate through the transesterification reaction or as the point when the by-product is no longer released.

The pressure during the transesterification reaction may be, for example, 0.01 $kg/cm^2$ or more, 0.05 $kg/cm^2$ or more, or 0.1 $kg/cm^2$ or more, and may be 0.5 $kg/cm^2$ or less, 0.3 $kg/cm^2$ or less, 0.2 $kg/cm^2$ or less, or 1.5 $kg/cm^2$ or less. The temperature during the transesterification reaction may be 140° C. or higher, 160° C. or higher, 180° C. or higher, or 200° C. or higher, and may be 300° C. or lower, 280° C. or lower, 270° C. or lower, 250° C. or lower, or 220° C. or lower. In addition, the transesterification reaction may be carried out under a nitrogen atmosphere. As a specific example, the transesterification reaction may be carried out at a pressure of 0.05 $kgf/cm^2$ to 0.2 $kgf/cm^2$ and a temperature of 180° C. to 280° C. under a nitrogen atmosphere.

The pressure and temperature conditions during the transesterification reaction may be appropriately adjusted according to the specific characteristics of a polyester to be produced, the ratio of each component, or process conditions. For example, the transesterification reaction may be carried out at a temperature of 180° C. or higher to smoothly remove ethylene glycol, a by-product formed during the transesterification reaction. In addition, it may be carried out at a temperature lower than the boiling point of the glycol component by 10° C. in order to reduce the loss of the glycol component for the substitution. As a specific example, when 1,4-butanediol is used as the glycol component, the temperature may be adjusted to 180° C. to 220° C. Alternatively, when 1,4-cyclohexanedimethanol is used, the temperature may be adjusted to 200° C. to 270° C.

The product of the transesterification reaction mainly comprises a bis(glycol) terephthalate and derivatives thereof in which ethylene glycol residues in bis(2-hydroxyethyl) terephthalate are substituted with other glycol residues.

According to an embodiment, the recycled bis(glycol) terephthalate obtained by the transesterification reaction comprises a compound represented by the following Formula 1.

[Formula 1]

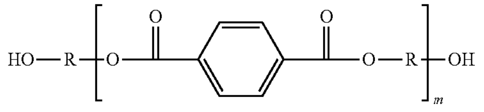

In Formula 1, —O—R—OH is a group derived from a glycol component having 3 or more carbon atoms, and m is an integer of 1 to 4.

For example, in Formula 1, R is a group derived from a glycol component having 3 or more carbon atoms, which may be an alkylene group having 3 to 10 carbon atoms or a group in which two or more identical or different alkylene groups having 3 to 10 carbon atoms are connected via an ether group or a carbonate group.

In addition, the recycled bis(glycol) terephthalate may comprise two or more compounds represented by Formula 1 or derivatives thereof.

Meanwhile, the product of the transesterification reaction stated above may comprise unreacted materials or by-products in addition to a bis(glycol) terephthalate.

As an example, the product of the transesterification reaction may comprise a component derived from recycled bis(2-hydroxyethyl) terephthalate used as a starting material. Specifically, the product of the transesterification reaction may comprise ethylene glycol and derivatives thereof.

The ethylene glycol derivative may be ethylene glycol or a compound having a residue thereof, for example, an ester of ethylene glycol. Specifically, the ethylene glycol derivative may comprise bis(2-hydroxyethyl) terephthalate, 2-hydroxyethyl terephthalate, 2-hydroxyethyl-4-hydroxybutyl terephthalate, bis(diethylene glycol) terephthalate, 2-hydroxydiethyl-diethylene glycol terephthalate, 4-hydroxybutyl-diethylene glycol terephthalate, ethylene glycol, and oligomers thereof. It may be mainly bis(2-hydroxyethyl) terephthalate.

The total content of ethylene glycol and derivatives thereof present in the product of the transesterification reaction stated above may be 20% by weight or less. Thus, the total content of ethylene glycol and derivatives thereof in the recycled bis(glycol) terephthalate may be 20% by weight or less. For example, the total content of ethylene glycol and derivatives thereof in the recycled bis(glycol) terephthalate may be 15% by weight or less, 10% by weight or less, or 5% by weight or less Accordingly, a polyester resin having high crystallinity can be produced using the recycled bis(glycol) terephthalate of the present invention.

Preparation of a Polyester Resin (Polycondensation Reaction)

The product of the transesterification reaction (i.e., a mixture containing a recycled bis(glycol) terephthalate) may be subjected to a polycondensation reaction to prepare a polyester resin.

That is, the process for preparing a polyester resin according to an embodiment of the present invention comprises (1) feeding at least one glycol component having 3 or more carbon atoms to a reactor; (2) feeding bis(2-hydroxyethyl) terephthalate to the reactor in a divided or continuous manner and carrying out a transesterification reaction; and (3) subjecting the product of the transesterification reaction to a polycondensation reaction, wherein the components fed to the reactor satisfy the above Relationship (1).

Referring to the following Reaction Scheme 2, the product of the transesterification reaction comprises a monomer or oligomer (dimer, trimer, or the like) of a bis(glycol) terephthalate. It may further comprise an excess glycol component remaining without participating in the transesterification reaction. The bis(glycol) terephthalate monomer or oligomer is subjected to a polycondensation reaction in the presence of a catalyst to prepare a polyester resin while a glycol is formed as a by-product of the polycondensation reaction.

In Reaction Scheme 2, m is an integer from 1 to 4, and n stands for the number of repeat units in the polymer chain.

The polycondensation reaction may be carried out, for example, by reacting the transesterification reaction product at a temperature of 150° C. to 300° C. and under a reduced pressure condition of 0.01 mmHg to 600 mmHg for 1 hour to 24 hours.

The temperature in the polycondensation reaction may be 150° C. to 300° C., specifically, 200° C. to 290° C., more specifically, 260° C. to 280° C. In addition, the pressure in the polycondensation reaction may be 0.01 mmHg to 600 mmHg, specifically, 0.05 mmHg to 200 mmHg, more specifically, 0.1 mmHg to 100 mmHg. As the reduced pressure condition is adopted in the polycondensation reaction, glycol, which is a by-product of the polycondensation reaction, can be removed from the system. If the pressure in the polycondensation reaction exceeds the range of 0.01 mmHg to 400 mmHg, the removal of by-products may be insufficient. In addition, if the temperature in the polycondensation reaction is lower than 150° C., a glycol as a by-product of the reaction cannot be effectively removed from the system; thus, the intrinsic viscosity of a final reaction product is low, resulting in a decrease in physical properties of the final polyester resin. If the temperature in the polycondensation reaction exceeds 300° C., the possibility of yellowing of a final polyester resin increases. In addition, the polycondensation reaction may be carried out for a necessary period of time, for example, an average residence time of 1 hour to 24 hours, until the intrinsic viscosity of a final reaction product reaches an appropriate level.

As the catalyst for the polycondensation reaction, for example, at least one selected from the group consisting of a titanium-based catalyst, a germanium-based catalyst, an antimony-based catalyst, an aluminum-based catalyst, and a tin-based catalyst may be used.

Examples of the titanium-based catalyst include tetraethyl titanate, acetyltripropyl titanate, tetrapropyl titanate, tetrabutyl titanate, 2-ethylhexyl titanate, octylene glycol titanate, triethanolamine titanate, acetylacetonate titanate, ethylacetoacetic ester titanate, isostearyl titanate, titanium dioxide, and the like. Examples of the germanium-based catalyst include germanium dioxide, germanium tetrachloride, germanium ethylene glycol oxide, germanium acetate, or combinations thereof. Specifically, germanium dioxide can be used as the germanium-based catalyst. Both crystalline and amorphous germanium dioxide may be used as the germanium dioxide, and glycol-soluble ones may also be used.

In addition, one or more glycol components and one or more acid components may be further introduced into the polycondensation reaction.

[Reaction Scheme 2]

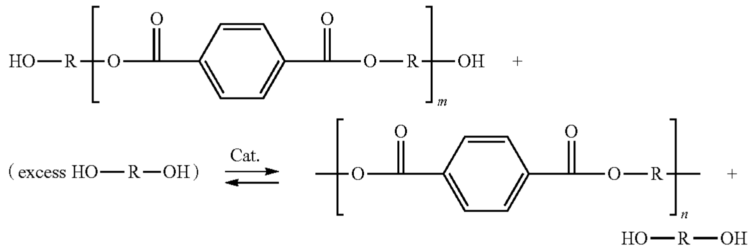

The specific type of the glycol component additionally introduced may be the same as the one or more glycol components fed to the reactor in step (1) above.

For example, the glycol component may be a glycol monomer (e.g., alkylene glycol) or a polymer glycol (e.g., polyether). Specifically, the glycol component may be selected from the group consisting of 1,3-propanediol, 1,4-butanediol, 1,4-cyclohexanedimethanol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 2,3-butanediol, 3-methyl-1,5-pentanediol, 3-methyl-2,4-pentanediol, 1,6-hexanediol, 1,2-cyclohexanediol, 1,4-cyclohexanediol, diethylene glycol, polyethylene glycol, polypropylene glycol, polytetramethylene glycol, polyhexamethylene glycol, copolymers of ethylene oxide and tetrahydrofuran, ethylene oxide-adducted polypropylene glycol, polycarbonate diol, polyneopentyl glycol, poly-3-methylpentanediol, and poly-1,5-pentanediol.

In addition, an acid component may be additionally introduced in step (1) or (3). For example, the acid component may be at least one selected from dicarboxylic acids and esters thereof. Specifically, the acid component may be selected from the group consisting of adipic acid, sebacic acid, succinic acid, isodecylsuccinic acid, maleic acid, fumaric acid, glutaric acid, azelaic acid, 1,4-cyclohexanedicarboxylic acid, 1,3-cyclohexanedicarboxylic acid, terephthalic acid, isophthalic acid, naphthalenedicarboxylic acid, diphenyldicarboxylic acid, 4,4'-stilbendicarboxylic acid, 2,5-furandicarboxylic acid, and 2,5-thiophenedicarboxylic acid.

Alternatively, ethylene glycol may be introduced as an additional glycol component, and terephthalic acid may be introduced as an additional acid component, into the polycondensation reaction, if necessary.

Polyester Resin

According to another aspect of the present invention, there is provided a polyester resin prepared by the above process.

That is, the polyester resin is prepared by the polycondensation of a recycled bis(glycol) terephthalate obtained by a transesterification reaction. Therefore, the polyester resin comprises units derived from the components derived from the recycled bis(glycol) terephthalate.

In addition, since the recycled bis(glycol) terephthalate contains unreacted glycol and acid components or by-products such as ethylene glycol, in addition to a bis(glycol) terephthalate, units derived from these components may be contained in the polyester resin through the subsequent polycondensation.

Specifically, the polyester resin may comprise units derived from one or more glycol components; and units derived from one or more acid components. The one or more glycol components may be glycol monomers or polymer glycols exemplified above. The one or more acid components may be an aliphatic dicarboxylic acid and an aromatic dicarboxylic acid exemplified above.

The glycol component and acid component that constitute the polyester resin are those derived from bis(2-hydroxyethyl) terephthalate and glycol components initially introduced for the preparation of the polyester resin, or a recycled bis(glycol) terephthalate prepared therefrom, and acid components additionally introduced.

The polyester resin may be a homopolymer or copolymer resin. As a specific example, the polyester resin may be at least one selected from polybutylene terephthalate (PBT), polytrimethylene terephthalate (PTT), polybutylene adipate-co-terephthalate (PBAT), polypropylene adipate-co-terephthalate (PPAT), polycyclohexane dimethyl terephthalate (PCT), and thermoplastic polyester elastomer (TPEE).

The polyester resin may have a total content of ethylene glycol residues and diethylene glycol residues at a certain level or lower. For example, the total content of ethylene glycol residues and diethylene glycol residues of the polyester resin may be 15% by mole or less, 10% by mole or less, 8% by mole or less, 7.5% by mole or less, 7% by mole or less, 6% by mole or less, 5% by mole or less, 4% by mole or less, or 3% by mole or less, relative to the number of moles of the entire glycol residues. In addition, the total content of ethylene glycol residues and diethylene glycol residues may be 0% by mole or more, 0.01% by mole or more, 0.02% by mole or more, or 0.03% by mole or more. The total content of ethylene glycol residues and diethylene glycol residues may be calculated by analyzing a spectrum of the polyester resin obtained by $^1$H-NMR. These residues may be derived from ethylene glycol, diethylene glycol, and their derivatives. As a specific example, the polyester resin may have a total content of ethylene glycol residues and diethylene glycol residues of 0.01% by mole to 10% by mole relative to the number of moles of the entire glycol residues when measured by $^1$H-NMR. Within the above content range, the crystallinity of the polyester resin may be enhanced so that thermal resistance and mechanical properties may be more excellent.

The polyester resin may have an intrinsic viscosity of 0.5 dl/g to 1.5 dl/g at 35° C. For example, the intrinsic viscosity of the polyester resin at 35° C. may be 0.5 dl/g or more, 0.55 dl/g or more, 0.6 dl/g or more, 0.7 dl/g or more, 0.8 dl/g or more, 0.9 dl/g or more, or 1.0 dl/g or more, and may be 1.5 dl/g or less, 1.4 dl/g or less, 1.3 dl/g or less, 1.2 dl/g or less, 1.1 dl/g or less, 1.0 dl/g or less, or 0.7 dl/g or less. As a specific example, the polyester resin may have an intrinsic viscosity of 0.55 to 1.1 dl/g or 0.6 to 0.7 dl/g at 35° C.

The polyester resin prepared by the above process may have a state such as chips, pellets, or powders before molding. It may also have a shape of a molded article formed by a separate molding process such as extrusion or injection, for example, a film or sheet form, or various injection part forms for automobiles, electrical and industrial purposes.

Accordingly, the present invention also provides an article, which comprises the polyester resin.

In particular, the polyester resin of the present invention can be utilized as high value-added engineering polyester products or biodegradable polyester products with low ethylene glycol components that affect ecotoxicity.

MODE FOR THE INVENTION

Hereinafter, a preferred embodiment is presented for the understanding of the present invention. However, the following examples are provided only to help easily understand the present invention, and the scope of the present invention is not limited thereby.

Preparation Example 1: Preparation of Bis(2-Hydroxyethyl) Terephthalate

A reactor made of stainless steel (SUS) was charged with 1,000 g of a waste polyester resin, 4,000 g of ethylene glycol, and 3.5 g of zinc acetate anhydride. The temperature inside the reactor was raised to 196° C., and depolymerization by a glycolysis reaction was carried out for 4 hours. The reaction resultant was cooled to 30° C., and the crystallization of bis(2-hydroxyethyl) terephthalate was carried out for 2 hours. The slurry of bis(2-hydroxyethyl) terephthalate and ethylene glycol thus obtained was subjected to solid-liquid separation in a centrifugal separator. Bis(2-hydroxyethyl) terephthalate obtained through centrifugation was washed twice with sufficient distilled water, and the residual solvent was removed in an oven to obtain about 1,100 g of a final product containing bis(2-hydroxyethyl) terephthalate.

Example 1

Step (1): Preparation of a Bis(Glycol) Terephthalate Through a Transesterification Reaction A 1-liter reactor for a transesterification reaction equipped with a column and a condenser that can be cooled by water was charged with 108.0 g of 1,4-butanediol (BD) as a glycol component and 94 mg of tetrabutyl titanate (TBT) as a reaction catalyst. Then, the pressure in the reactor was adjusted to 0.1 kg/cm$^2$ by flowing nitrogen, and the temperature was raised while the pressure was maintained with stirring. When the temperature in the reactor reached about 200° C., while the temperature was raised to 220° C. over 3 hours, 127.0 g of bis(2-hydroxyethyl) terephthalate (BHET) obtained in Preparation Example 1 was fed as divided into 5 portions to carry out a transesterification reaction. Glycols as by-products were discharged through the column and condenser during the reaction. Even upon completion of the addition of BHET, the transesterification reaction was continued while maintaining 220° C. until the discharge of glycols stopped. Upon completion of the transesterification reaction, nitrogen in the pressurized reactor was released to the outside to lower the pressure in the reactor to normal pressure, and the resultant (a mixture containing bis(2-hydroxyethyl) terephthalate) in the reactor was then transferred to a 0.5-liter reactor capable of a reaction under vacuum.

Step (2): Preparation of a Polyester Resin Through a Polycondensation Reaction

The pressure of the reactor was reduced from normal pressure to 5.0 Torr (absolute pressure: 5 mmHg) over 30 minutes. At the same time, the temperature of the reactor was raised to 245° C. over 1 hour, and a polycondensation reaction was carried out while the pressure of the reactor was maintained at 1 Torr (absolute pressure: 1 mmHg) or less. At the beginning of the polycondensation reaction, the stirring speed might be set high. As the polycondensation reaction proceeded, the glycol component as a by-product was discharged from the reactor. When the stirring power was weakened due to the increase in the viscosity of the reactants or the temperature of the reactants was elevated above the set temperature, the stirring speed was appropriately adjusted. The polycondensation reaction was carried out until the intrinsic viscosity (IV) of the mixture (melt) in the reactor reached 0.75 to 0.85 dl/g. When the intrinsic viscosity of the mixture in the reactor reached the desired level, the mixture was then discharged to the outside of the reactor to form strands. They were solidified with a cooling liquid and then granulated to have an average weight of about 12 to 14 mg to obtain 109.7 g of a polyester resin.

Example 2

A polyester resin was obtained through the same procedure as in Example 1, except that in step (1), 111.7 g of 1,4-cyclohexanedimethanol (CHDM) was employed as a glycol component, 127.0 g of BHET was fed as divided into 6 portions, and the final temperature during the transesterification reaction was set to 260° C.; and that in step (2), the final temperature during the polycondensation reaction was adjusted to 295° C.

Example 3

A polyester resin was obtained through the same procedure as in Example 1, except that in step (1), 127.0 g of BHET was fed as divided into 8 portions.

Example 4

A polyester resin was obtained through the same procedure as in Example 1, except that in step (1), 127.0 g of BHET was fed as divided into 12 portions.

Example 5

A polyester resin was obtained through the same procedure as in Example 1, except that in step (1), 127.0 g of BHET was dissolved in 850 g of purified water at 90° C. to prepare an aqueous BHET solution of 13% by weight, and the aqueous BHET solution was then continuously fed at a constant rate of 4.07 g/minute over 4 hours using a dropping funnel.

Example 6

A polyester resin was obtained through the same procedure as in Example 1, except that in step (1), 93.1 g of 1,3-propanediol (PDO) was employed as a glycol component, 127.0 g of BHET was fed as divided into 4 portions, and the final temperature during the transesterification reaction was set to 200° C.; and that in step (2), the final temperature during the polycondensation reaction was adjusted to 245° C.

Example 7

A polyester resin was obtained through the same procedure as in Example 1, except that in step (1), 95.6 g of 1,4-butanediol (BD) and 87.9 g of polytetramethylene glycol (PTMG, Mn 1,000) were employed as a glycol component and the final temperature during the transesterification reaction was set to 220° C.; and that in step (2), the final temperature during the polycondensation reaction was adjusted to 245° C.

Example 8

A polyester resin was obtained through the same procedure as in Example 7, except that in step (1), 95.6 g of 1,4-butanediol (BD) and 87.9 g of poly-1,3-propylene glycol (PO3G, Mn 1,000) were employed as a glycol component.

Example 9

A polyester resin was obtained through the same procedure as in Example 7, except that in step (1), 95.6 g of 1,4-butanediol (BD) and 111.3 g of ethylene oxide-adducted polypropylene glycol (EO-PPG, Mn 2,400) were employed as a glycol component.

Example 10

A polyester resin was obtained through the same procedure as in Example 1, except that in step (1), 72.0 g of 1,4-butanediol (BD) was employed as a glycol component, 63.5 g of BHET was fed as divided into 4 portions, and 36.5 g of adipic acid (AA) was employed as an additional acid component.

Example 11

A polyester resin was obtained through the same procedure as in Example 10, except that in step (1), 60.8 g of 1,3-propanediol (PDO) was employed as a glycol component.

Comparative Example 1

A polyester resin was obtained through the same procedure as in Example 1, except that in step (1), BHET was fed at one time together with 1,4-butanediol (BD) at the beginning.

Comparative Example 2

A polyester resin was obtained through the same procedure as in Comparative Example 1, except that in step (1), the amount of 1,4-butanediol (BD) employed was increased to 180.1 g.

Comparative Example 3

A polyester resin was obtained through the same procedure as in Example 2, except that in step (1), BHET was fed at one time together with 1,4-cyclohexanedimethanol (CHDM) at the beginning.

Comparative Example 4

A polyester resin was obtained through the same procedure as in Example 7, except that in step (1), BHET was fed at one time together with polytetramethylene glycol (PTMG, Mn 1,000) at the beginning.

Comparative Example 5

A polyester resin was obtained through the same procedure as in Example 6, except that in step (1), BHET was fed at one time together with 1,3-propanediol (PDO) at the beginning.

Comparative Example 6

A polyester resin was obtained through the same procedure as in Example 10, except that in step (1), BHET was fed at one time together with 1,4-butanediol (BD) and adipic acid (AA) at the beginning.

Comparative Example 7

A polyester resin was obtained through the same procedure as in Example 10, except that in step (1), BHET was fed at one time together with 1,3-propanediol (PDO) and adipic acid (AA) at the beginning.

The components used in the above Examples and Comparative Examples and their amounts employed are shown in Tables 1 and 2 below.

In addition, the glycol/rBHET ratio (G/B) of the following Relationship (1) and the rBHET introduction ratio (R) of the following Relationship (2) were calculated and shown in Table 1 below.

$$1.0 \leq G/B \leq 3.5 \quad (1)$$

In Relationship (1), G is the total number of moles of the at least one glycol component, and B is the total number of moles of the bis(2-hydroxyethyl) terephthalate.

$$R = G \times \frac{N}{B} \quad (2)$$

In Relationship (2), G is the total number of moles of the at least one glycol component, B is the total number of moles of the bis(2-hydroxyethyl) terephthalate, and N is the number of divided introductions of the bis(2-hydroxyethyl) terephthalate.

Test Example 1: Purity of r-BHET

The purity of r-BHET obtained in Preparation Example 1 was measured by diluting 0.01 g of the sample in 20 ml each of methanol or chloroform using liquid chromatography. As a result of analyzing the component content (area %) in the entire r-BHET by integrating the peak areas through the measured spectrum, 75-80% of BHET and 20-25% of other oligomers, DEG derivatives, and unreacted monomers were confirmed.

Test Example 2: Content of EG and DEG Residues

Each polyester resin was dissolved in a $CDCl_3$ solvent at a concentration of 3 mg/ml, whose $^1$H-NMR spectrum was obtained at 25° C. using a nuclear magnetic resonance apparatus (JEOL, 600 MHz FT-NMR). The total content (% by mole) of ethylene glycol residues and diethylene glycol residues based on the total number of moles of residues derived from all glycols (EG, DEG, BD, PDO, PTMG, PO3G, EO-PPG, and the like) was calculated by analyzing the above spectra.

Test Example 3: Intrinsic Viscosity

A polyester resin was dissolved at a concentration of 0.12% in orthochlorophenol (OCP) at 150° C. to obtain a solution, and an Ubbelohde viscometer was used in a constant temperature bath at 35° C. to measure intrinsic viscosity. Specifically, the temperature of the viscous tube was maintained at 35° C., and the time (efflux time) required for the solvent to pass between specific internal sections of the viscous tube and the time required for the solution to pass to obtain specific viscosity, which was used to calculate intrinsic viscosity.

Test Example 4: Tm and $\Delta H_f$

Each polyester resin was dried under a reduced pressure at 50° C. for 15 hours, melted, and quenched, which was then heated at 10° C./minute in a differential scanning calorimeter (DSC, TA Instruments) for testing. The highest point of the endothermic peak by resin melting was taken as the melting point (Tm), and the heat of fusion ($\Delta H_f$) was calculated as the area of the endothermic peak.

The test results are shown in Tables 1 and 2 below.

TABLE 1

| | | Molecular weight | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|---|
| Acid component (g) | rBHET | 254.24 | 127.0 | 127.0 | 127.0 | 127.0 | 127.0 | 127.0 | 127.0 | 127.0 | 127.0 | 63.5 | 63.5 |
| | AA | 146.14 | — | — | — | — | — | — | — | — | — | 36.5 | 36.5 |
| Glycol component (g) | BD | 90.12 | 108.0 | — | 90.0 | 90.0 | 90.0 | — | 95.6 | 95.6 | 95.6 | 72.0 | — |
| | PDO | 76.09 | — | — | — | — | — | 93.1 | — | — | — | — | 60.8 |
| | CHDM | 144.21 | — | 111.7 | — | — | — | — | — | — | — | — | — |
| | PTMG | 1000 | — | — | — | — | — | — | 87.9 | — | — | — | — |
| | PO3G | 1000 | — | — | — | — | — | — | — | 87.9 | — | — | — |
| | EO-PPG | 2,400 | — | — | — | — | — | — | — | — | 111.3 | — | — |
| G/B | | | 2.40 | 1.55 | 2.00 | 2.00 | 2.00 | 2.45 | 2.30 | 2.30 | 2.22 | 1.60 | 1.60 |
| Number of divided feedings of rBHET | | | 5 | 6 | 8 | 12 | Continuous feeding | 4 | 4 | 4 | 4 | 4 | 4 |
| R | | | 12.0 | 9.3 | 16.0 | 24.0 | — | 9.80 | 9.20 | 9.20 | 8.90 | 6.40 | 6.40 |
| Fed amount (g) | | | 235.0 | 238.6 | 217.0 | 217.0 | 217.0 | 220.1 | 389.0 | 388.0 | 381.0 | 172.0 | 160.8 |
| Yield (g) | | | 109.7 | 135.2 | 109.5 | 109.9 | 110.3 | 102.8 | 235.0 | 234.0 | 242.0 | 106.8 | 99.8 |
| IV (dl/g) | | | 0.84 | 0.65 | 0.79 | 0.83 | 0.86 | 0.76 | 1.30 | 1.20 | 1.16 | 1.19 | 1.02 |
| EG and DEG (% by mole) | | | 5.3 | 9.9 | 4.4 | 3.3 | 2.9 | 5.6 | 4.7 | 4.8 | 5.0 | 7.4 | 6.2 |
| Tm | | | 217.3 | 280.7 | 217.6 | 217.9 | 219.3 | 221.2 | 196.5 | 198.4 | 209.4 | 118.6 | 134.0 |
| $\Delta H_f$ (J $g^{-1}$) | | | 50.3 | 38.7 | 50.6 | 50.9 | 52.0 | 49.2 | 21.5 | 23.4 | 29.4 | 10.1 | 13.0 |

TABLE 2

| | | Molecular weight | C. Ex. 1 | C. Ex. 2 | C. Ex. 3 | C. Ex. 4 | C. Ex. 5 | C. Ex. 6 | C. Ex. 7 |
|---|---|---|---|---|---|---|---|---|---|
| Acid component (g) | rBHET | 254.24 | 127.0 | 127.0 | 127.0 | 127.0 | 127.0 | 63.5 | 63.5 |
| | AA | 146.14 | — | — | — | — | — | 36.5 | 36.5 |
| Glycol component (g) | BD | 90.12 | 108.0 | 180.1 | — | 95.6 | — | 72.0 | — |
| | PDO | 76.09 | — | — | — | — | 93.1 | — | 60.8 |
| | CHDM | 144.21 | — | — | 111.7 | — | — | — | — |
| | PTMG | 1000 | — | — | — | 137.9 | — | — | — |
| | PO3G | 1000 | — | — | — | — | — | — | — |
| | EO-PPG | 2,400 | — | — | — | — | — | — | — |
| G/B | | | 2.40 | 4.00 | 1.55 | 2.40 | 2.45 | 1.60 | 1.60 |
| Number of divided feedings of rBHET | | | 1 | 1 | 1 | 1 | 1 | 1 | 1 |
| R | | | 2.40 | 4.00 | 1.55 | 2.40 | 2.45 | 1.60 | 1.60 |
| Fed amount (g) | | | 235.0 | 307.1 | 238.6 | 360.5 | 220.1 | 172.0 | 160.8 |
| P amount (g) | | | 108.5 | 109.3 | 131.1 | 234.2 | 102.5 | 105.4 | 99.3 |
| IV (dl/g) | | | 0.62 | 0.72 | 0.55 | 0.95 | 0.68 | 1.01 | 0.95 |
| EG and DEG (% by mole) | | | 22.2 | 12.2 | 28.8 | 18.4 | 17.1 | 23.1 | 22.4 |
| Tm | | | 207.9 | 212.9 | 269.6 | 188.8 | 214.5 | 109.5 | 124.8 |
| $\Delta H_f$ (J $g^{-1}$) | | | 37.2 | 45.2 | 22.8 | 10.7 | 39.6 | 2.7 | 3.3 |

As can be seen from Tables 1 and 2, in Examples 1 to 11 according to the present invention, in which the transesterification reaction was carried out while rBHET was fed in a divided or continuous manner under the condition of the rBHET introduction ratio (R) being 5 or more, the total content of EG and DEG residues was as low as 10% by mole or less. In contrast, in Comparative Examples 1 to 7 in which the transesterification reaction was carried out while rBHET was fed at one time, the total content of EG and DEG residues exceeded 10% by mole.

As a result, the polyester resins of the Examples had a melting point ($T_m$) and a heat of fusion ($\Delta H_f$) higher than those of the polyester resins of Comparative Examples prepared at the same glycol/rBHET ratio (G/B), indicating that they had excellent crystallinity.

The invention claimed is:

1. A process for preparing a bis(glycol) terephthalate, which comprises:

(1) feeding at least one glycol component having 3 or more carbon atoms to a reactor; and (2) feeding bis(2-hydroxyethyl) terephthalate to the reactor in a divided manner and carrying out a transesterification reaction, wherein the following Relationship (1) is satisfied:

$$1.0 \leq G/B \leq 3.5 \quad (1)$$

in Relationship (1), G is the total number of moles of the at least one glycol component, and B is the total number of moles of the bis(2-hydroxyethyl) terephthalate, and wherein the bis(2-hydroxyethyl) terephthalate is introduced into the transesterification reaction in step (2) in a divided manner of two or more times, and the introduction ratio (R) of bis(2-hydroxyethyl) terephthalate according to Relationship (2) is 5 or more:

$$R = G \times \frac{N}{B} \quad (2)$$

in Relationship (2), G is the total number of moles of the at least one glycol component, B is the total number of moles of the bis(2-hydroxyethyl) terephthalate, and N is the number of divided introductions of the bis(2-hydroxyethyl) terephthalate.

2. The process for preparing a bis(glycol) terephthalate of claim 1, wherein the glycol component in step (1) is at least one selected from glycol monomers having 3 to 10 carbon atoms and having a molecular weight of less than 250 and polymeric glycols having a number average molecular weight of 400 to 5,000.

3. The process for preparing a bis(glycol) terephthalate of claim 1, wherein, in step (1), at least one acid component selected from dicarboxylic acids and esters and anhydrides thereof is additionally fed into the reactor.

4. The process for preparing a bis(glycol) terephthalate of claim 3, wherein the dicarboxylic acid comprises an aliphatic dicarboxylic acid.

5. The process for preparing a bis(glycol) terephthalate of claim 1, wherein the purity of the bis(2-hydroxyethyl) terephthalate fed in step (2) is 60% to 90%.

6. The process for preparing a bis(glycol) terephthalate of claim 1, wherein the bis(2-hydroxyethyl) terephthalate is obtained by the depolymerization of waste polyester.

7. The process for preparing a bis(glycol) terephthalate of claim 1, wherein the introduction of the bis(2-hydroxyethyl) terephthalate is carried out while ethylene glycol as a by-product is removed in a nitrogen atmosphere at a temperature of 180° C. to 280° C.

8. A process for preparing a polyester resin, which comprises:

(1) feeding at least one glycol component having 3 or more carbon atoms to a reactor;

(2) feeding bis(2-hydroxyethyl) terephthalate to the reactor in a divided or continuous manner and carrying out a transesterification reaction; and (3) subjecting the product of the transesterification reaction to a polycondensation reaction, wherein the following Relationship (1) is satisfied:

$$1.0 \leq G/B \leq 3.5 \quad (1)$$

in Relationship (1), G is the total number of moles of the at least one glycol component, and B is the total number of moles of the bis(2-hydroxyethyl) terephthalate, wherein the bis(2-hydroxyethyl) terephthalate is introduced into the transesterification reaction in step (2) in a divided manner of two or more times, and the introduction ratio (R) of bis(2-hydroxyethyl) terephthalate according to Relationship (2) is 5 or more:

$$R = G \times \frac{N}{B} \quad (2)$$

in Relationship (2), G is the total number of moles of the at least one glycol component, B is the total number of moles of the bis(2-hydroxyethyl) terephthalate, and N is the number of divided introductions of the bis(2-hydroxyethyl) terephthalate.

9. The process for preparing a polyester resin of claim 8, wherein the at least one glycol component in step (1) is selected from the group consisting of 1,3-propanediol, 1,4-butanediol, 1,4-cyclohexanedimethanol, 2-methyl-1,3-propanediol, 2-methylene-1,3-propanediol, 2-ethyl-1,3-propanediol, 2-isopropyl-1,3-propanediol, 2,2-dimethyl-1,3-propanediol, 2,3-butanediol, 3-methyl-1,5-pentanediol, 3-methyl-2,4-pentanediol, 1,6-hexanediol, 1,2-cyclohexanediol, 1,4-cyclohexanediol, diethylene glycol, polyethylene glycol, polypropylene glycol, polytetramethylene glycol, polyhexamethylene glycol, copolymers of ethylene oxide and tetrahydrofuran, ethylene oxide-adducted polypropylene glycol, polycarbonate diol, polyneopentyl glycol, poly-3-methylpentanediol, and poly-1,5-pentanediol.

10. The process for preparing a polyester resin of claim 8, wherein an acid component is additionally introduced in step (1) or (3), and the acid component is selected from the group consisting of adipic acid, sebacic acid, succinic acid, isodecylsuccinic acid, maleic acid, fumaric acid, glutaric acid, azelaic acid, 1,4-cyclohexanedicarboxylic acid, 1,3-cyclohexanedicarboxylic acid, terephthalic acid, isophthalic acid, naphthalenedicarboxylic acid, diphenyldicarboxylic acid, 4,4'-stilbendicarboxylic acid, 2,5-furandicarboxylic acid, and 2,5-thiophenedicarboxylic acid.

* * * * *